US006278012B1

(12) United States Patent
Hörold et al.

(10) Patent No.: US 6,278,012 B1
(45) Date of Patent: *Aug. 21, 2001

(54) PROCESS FOR PREPARING PHOSPHINATE ESTERS

(75) Inventors: Sebastian Hörold, Erftstadt; Norbert Weferling; Heinz-Peter Breuer, both of Hürth; Martin Sicken, Köln, all of (DE)

(73) Assignee: Clariant GmbH, Frankfurt (DE)

( * ) Notice: Subject to any disclaimer, the term of this patent is extended or adjusted under 35 U.S.C. 154(b) by 0 days.

This patent is subject to a terminal disclaimer.

(21) Appl. No.: 09/577,465

(22) Filed: May 24, 2000

(30) Foreign Application Priority Data

May 25, 1999 (DE) ............................................. 199 23 617

(51) Int. Cl.⁷ ................................. C07F 9/02; C07F 9/22
(52) U.S. Cl. .......................... 558/110; 558/137; 558/167; 558/171; 558/177; 558/179; 558/180; 558/184; 562/8
(58) Field of Search .................................. 558/110, 137; 562/8

(56) References Cited

U.S. PATENT DOCUMENTS

| 4,521,348 | 6/1985 | Finke et al. . |
| 5,399,428 | 3/1995 | Asrar . |
| 6,090,968 | * 7/2000 | Hörold et al. ........................ 558/137 |

FOREIGN PATENT DOCUMENTS 26 52 007   5/1978 (DE) .

1 517 865   7/1978 (GB) .

OTHER PUBLICATIONS

Houben–Weyl, vol. 12/1, pp. 258–259 (1952).
Houben–Weyl, vol. 12/1, p. 230, K.K. Kharullin, T.I. Sobchuk, A.N. Pudovik, Zh. (1952).
Zh. Obshch.Khim. 37, 710 (1967).
Houben–Weyl, vol. 12/1, pp. 232&306 (1952).
Derwent Patent Family Abstract for DE 26 52 007, No. 1978 – 36801A (1978).

* cited by examiner

*Primary Examiner*—Deborah C. Lambkin
(74) *Attorney, Agent, or Firm*—Andrew Pang; Scott E. Hanf

(57) ABSTRACT

The present invention relates to a process for the preparation of phosphinic acid esters, which comprises
 a) reacting elemental yellow phosphorus with alkylating agents in the presence of a base to give a mixture which comprises, as principal constituents, the (metal) salts of alkylphosphonous, phosphorous and hypophosphorous acids,
 b) esterifying the principal constituents of the mixture from a) to give an ester mixture,
 c) isolating the ester of the alkylphosphonous acid from the ester mixture,
 d) adding the resultant ester of the alkylphosphonous acid onto an olefin containing a functional group.

The invention likewise relates to the use of the phosphinic acid esters prepared by this process, inter alia as flame retardants and precursors for further syntheses.

37 Claims, No Drawings

PROCESS FOR PREPARING PHOSPHINATE ESTERS

BACKGROUND OF THE INVENTION

The present invention relates to a process for the preparation of phosphinic acid esters and to the use of the products prepared by this process.

Phosphinic acid esters are valuable synthetic building blocks and can be used, for example, for the preparation of polymers and plastics in order to obtain flame-resistant materials.

Thus, DE 26 52 007 A1 describes flame-resistant epoxy resins through incorporation of carboxyl-functional phosphinic acids. U.S. Pat. No. 5,399,428 A1 describes flame-resistant linear polyesters through incorporation of carboxyl-functional phosphinic acids.

DE 25 40 283 A1 describes the addition of phosphines onto α,β-unsaturated carboxylic acids in the presence of aqueous hydrochloric acid, followed by oxidation.

DE 28 49 003 describes the preparation of phosphorus-containing cyanohydrin derivatives by the addition of phosphonous acid esters onto acroleincyanohydrin derivatives.

Phosphinic acid esters are obtained by adding phosphonous acid monoesters onto 1-olefins in the presence of peroxidic catalysts. However, the yields are only low. The addition of phosphonous acid monoesters onto activated double bonds in the presence of alkoxides as catalyst proceeds better. Suitable unsaturated compounds are α,β-unsaturated carboxylic acid esters or nitriles, α,β-unsaturated ketones and alkyl vinyl sulfones and vinyl acetate (Houben-Weyl, Volume 12/1, pp. 258–259).

The phosphonous acid monoesters themselves are prepared from phosphonous acid dihalides by reaction with alcohols or by hydrolysis and subsequent esterification.

Functional phosphinic acids are obtained by reacting phosphonous acid dihalides (dihalophosphines) with activated olefinic compounds, such as, for example, acrylic or methacrylic acid derivatives, followed by hydrolysis (Houben-Weyl, Volume 12/1, p. 230; K. K. Khairullin, T. I. Sobchuk, A. N. Pudovik, Zh. Obshch. Khim. 37, 710 (1967)). Byproducts formed in the hydrolysis with organic acids are their halides.

In addition, phosphonous acid dihalides can be reacted with alkyl halides in the presence of aluminum chloride (Houben-Weyl, Volume 12/1, p. 232).

Phosphinic acid esters can also be prepared from dialkyl phosphonites by the Michaelis-Arbuzov reaction. The abovementioned dialkyl phosphonites are in turn prepared from phosphonous acid dihalides and hydroxyl compounds.

The abovementioned phosphonous acid dihalides, which can be employed as starting materials for other syntheses, for example methyldichlorophosphine, have hitherto themselves been prepared in a complex synthesis from phosphorus trihalides and alkyl halides in the presence of aluminum chloride (Houben-Weyl, Volume 12/1, p. 306). The reaction is highly exothermic and can only be controlled with difficulty in industry. In addition, various byproducts are formed which, like some of the abovementioned starting materials, are toxic and/or corrosive, i.e. are highly undesired.

SUMMARY OF THE INVENTION

There is therefore a need for a process for the preparation of phosphinic acid esters which can be carried out in a simple manner and in which uniform products are obtained in high yield. A process of this type should also be significantly superior to the processes known hitherto in environmental terms.

The invention thus has the object of providing a process for the preparation of phosphinic acid esters which avoids the abovementioned disadvantages and starts from elemental yellow phosphorus as starting material.

DESCRIPTION OF THE PREFERRED EMBODIMENTS

This object is achieved by a process of the type mentioned at the outset which comprises a) reacting elemental yellow phosphorus with alkylating agents in the presence of a base to give a mixture which comprises, as principal constituents, the (metal) salts of alkylphosphonous, phosphorous and hypophosphorous acids, b) esterifying the principal constituents of the mixture from a) to give an ester mixture, c) isolating the ester of the alkylphosphonous acid from the ester mixture, d) adding the resultant ester of the alkylphosphonous acid onto an olefin containing a functional group.

The process according to the invention has considerable advantages over the processes known hitherto since it has a positive balance in the product distribution and at the same time avoids the phosphine and phosphonous acid dihalide starting materials, which are regarded as undesired, and in addition produces no halogenated organic byproducts.

The alkylating agents are preferably alkyl halides, dialkyl sulfates, trialkyl phosphates, dialkyl carbonates and/or formic acid ortho-esters.

The alkylating agents employed are particularly preferably methyl chloride, methyl bromide and/or dimethyl sulfate.

The bases are preferably hydroxides, carbonates, bicarbonates, amides, alkoxides and/or amine bases, such as, for example, amines and ammonia.

The reaction in step a) is preferably carried out in a two-phase system comprising aqueous alkali or alkaline-earth metal hydroxide or mixtures thereof and an organic solvent.

The organic solvents employed in step a) are preferably straight-chain or branched alkanes, alkyl-substituted aromatic solvents, water-immiscible or only partially water-miscible alcohols or ethers, alone or in combination with one another.

The organic solvent employed is particularly preferably toluene, alone or in combination with alcohols.

The reaction can, if desired, also be carried out in a non-aqueous system, for example by using solid sodium hydroxide or amines.

The reaction is preferably carried out in the presence of a phase-transfer catalyst.

The phase-transfer catalyst is preferably a tetraalkylphosphonium halide, triphenylalkylphosphonium halide or tetraorganylammonium halide.

The temperature during the reaction is preferably from −20 to +80° C.

The temperature is particularly preferably from −10 to +30° C.

The reaction is preferably carried out under a pressure of from 0 to 10 bar.

Step a) of the process according to the invention is preferably carried out by suspending or dissolving the yellow phosphorus in a solvent or solvent mixture and then reacting it with an alkyl halide and a compound of the formula MOH or M' (OH)$_2$ or mixtures thereof, where M is an alkali metal and M' is an alkaline-earth metal.

The yellow phosphorus and the alkyl halide are preferably reacted with one another in a molar ratio of from 1:1 to 1:3, where the molar ratio of yellow phosphorus to the compound of the formula MOH or M' (OH)$_2$ is from 1:1 to 1:5.

The principal constituents of the mixture from a) are preferably esterified in step b) using a linear or branched alcohol of the general formula R—OH, where R is a linear or branched alkyl radical having 1 to 10 carbon atoms.

In another preferred embodiment of the process according to the invention, the principal constituents of the mixture from a) are converted into a mixture of alkylphosphonous, phosphorous and hypophosphorous acids using mineral acids, with the (metal) salts of the mineral acids simultaneously being precipitated, and the mixture of these acids subsequently being esterified.

The water formed during the esterification is preferably removed by azeotropic distillation.

In other words, the esterification of the phosphonous acid to the corresponding monoester can be achieved by reaction with relatively high-boiling alcohols with removal of the resultant water by azeotropic distillation.

The precipitation of the metal salts, usually the alkali or alkaline-earth metal mineral salts, is preferably carried out here by replacement of the solvent water by the alcohol to be used in reaction step b).

The alkali or alkaline-earth metal mineral salt which has already precipitated is preferably filtered off before the esterification.

The alcohol is preferably n- or i-butanol, n-hexanol, ethylhexanol and/or amyl alcohol.

The mineral acid is preferably hydrochloric acid, sulfuric acid and/or phosphoric acid.

The mineral acid is particularly preferably hydrochloric acid.

The phosphines formed in small amounts during step a) are preferably removed by oxidation.

Hydrogen peroxide is preferably used as oxidant.

The ester of the alkylphosphonous acid is preferably removed by distillation in step c). The ester of the alkylphosphonous acid is preferably n-butyl methylphosphonite, isobutyl methylphosphonite, n-hexyl methylphosphonite, 2-ethylhexyl methylphosphonite and/or amyl methylphosphonite.

The addition reaction in step d) is preferably carried out in the presence of catalysts.

The catalysts here are preferably basic catalysts. Alternatively, it is also possible to employ acids or cationic free-radical initiators.

The basic catalysts are preferably alkali metal and/or alkaline-earth metal alkoxides.

The olefins containing functional groups are preferably α,β-unsaturated carboxylic acid esters, amides or nitriles, α,β-unsaturated ketones, alkyl vinyl sulfones or vinyl acetate.

The olefins containing functional groups are preferably α,β-unsaturated carboxylic acid esters of aliphatic or cycloaliphatic alcohols having 1 to 20 carbon atoms or α,β-unsaturated carboxylic acid esters of polyhydric alcohols having 2 to 4 hydroxyl groups and 2 to 20 carbon atoms.

The olefins containing functional groups are preferably acrylic acid derivatives of the general formula (I)

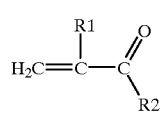

(I)

where R1 is CH$_3$ or H, and R2 is an ester group of a monohydric or polyhydric alcohol having 1 to 12 carbon atoms or an amine group.

The olefins containing functional groups are preferably acroleincyanohydrin compounds of the formula (II)

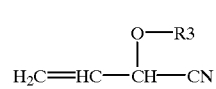

(II)

where R3=acetyl or propionyl.

The olefins containing functional groups are preferably itaconic acid derivatives of the general formula (III) where R'=alkyl group having 1–12 carbon atoms.

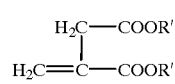

(III)

The olefin containing a functional group is preferably hydroxyethyl acrylate, methyl acrylate, ethyl acrylate, butyl acrylate, 2-ethylhexyl acrylate, hydroxyethyl methacrylate, methyl methacrylate, ethyl methacrylate, dimethyl itaconate, diethyl itaconate or acroleincyanohydrin acetate.

The alkylphosphonous acid is preferably methanephosphonous acid.

The invention also relates to the use of the functional phosphinic acids prepared by the process according to the invention as reactive flame retardants for polymers.

The invention also relates to the use of the functional phosphinic acids prepared by the process according to the invention as reactive flame retardants for thermoplastic polymers, such as polyethylene terephthalate, polybutylene terephthalate or polyamide.

The invention also relates to the use of the functional phosphinic acids prepared by the process according to the invention as reactive flame retardants for thermosetting resins, such as unsaturated polyester resins, epoxy resins, polyurethanes or acrylates.

The invention also relates to the use of the functional phosphinic acids prepared by the process according to the invention as precursors for the chemical synthesis of other phosphorus-containing compounds.

Surprisingly, it has been found that elemental yellow phosphorus can, after step a) of the process according to the invention, be reacted with alkylating agents in the two-phase system (organic solvent/base) and, if desired, in the presence of a (phase-transfer) catalyst under extremely mild conditions to give the (metal) salt of the corresponding alkylphosphonous acid RP(:O)HOH.

In addition, small amounts of dialkylphosphinic acids, trialkylphosphine oxide R$_3$P(:O), dialkylphosphine oxide and unidentified phosphorus compounds may be formed; these can be removed from the product mixture in the usual manner. A further byproduct formed is hydrogen, which can easily be separated off from the reaction mixture. The abovementioned dialkylphosphinic acids can be separated off from the reaction mixture and employed or further processed elsewhere.

Surprisingly, neither phosphine ($PH_3$) nor alkylphosphines ($RPH_2$, $R_2PH$) are formed in significant amounts in the process according to the invention. Through the choice of suitable reaction conditions—such as the addition of small amounts of alcohols to the organic phase—the formation of all unidentified phosphorus-containing byproducts is minimized to a surprisingly low content of a few mol % of the yellow phosphorus employed, in favor of the main product, the (metal) salts of the alkylphosphonous acid.

The process according to the invention can be carried out, for example, by initially introducing the solvent together with the phase-transfer catalyst and, if necessary, warming the mixture to above the melting point of the yellow phosphorus, then adding the elemental (yellow) phosphorus, cooling the mixture to temperatures of, for example, from −10 to +30° C. with vigorous stirring, and subsequently adding the alkylating agent.

The reaction is initiated by addition of the base. When the reaction is complete, the reaction system can be diluted, for example with water, and the readily volatile components ($H_2$, $PH_3$, $RPH_2$, $R_2PH$ and excess alkylating agent, etc.) are subsequently removed.

This gives a base-containing/organic two-phase system, whose phases are separated. The contents from the phases are determined analytically.

The reactants can also be combined in a different sequence, for example by introducing them continuously into a reactor (pressure tube, pressure reactor or cascade) in the above-defined molar ratio and removing them from the reactor again after a residence time of from 0.5 to 2 hours. The organic phase obtained after the phase separation, which still contains the majority of any phase-transfer catalyst employed, is advantageously recycled.

The isolation of the pure alkylphosphonous acids from the mixture is carried out in a particularly simple manner via the corresponding esters, which, in contrast to the salts and acids of the alkylphosphonous acids, can be isolated from the mixture in a gentle manner by distillation. Although all other compounds present in the mixture are also partially esterified in steps b) and c) of the process according to the invention, they do not, however, form readily distillable products, and consequently the removal of the alkylphosphonous acid esters is achieved in surprisingly complete and pure form.

The invention is explained by the examples below:

EXAMPLES

Example 1 a1) Reaction of yellow phosphorus with alkyl halide

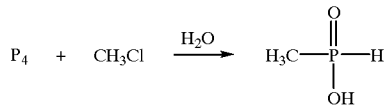

A solution of 26.1 g (0.05 mol) of tributylhexadecylphosphonium bromide in 1000 ml of toluene was introduced into a 5 l stainless-steel pressure reactor and preheated to 60° C. After 62 g (2 mol) of yellow phosphorus had been added, the mixture was cooled to −10° C. with vigorous stirring, and 202 g (4 mol) of methyl chloride were then condensed in. 400 g of 50% aqueous sodium hydroxide solution were then metered in over the course of 2 hours, during which the temperature was held at −10° C. 400 g of water were added over the course of a further hour, the mixture was then stirred for a further hour and warmed to room temperature, and the reactor was subsequently decompressed via combustion. Two homogeneous liquid phases were obtained, which were separated and analyzed.

The aqueous phase (weight: 920 g) contained 65.6 mol % of methylphosphonous acid, 14.9 mol % of phosphorous acid, 13.7 mol % of hypophosphorous acid and 2.8 mol % of dimethylphosphinic acid in the form of their sodium salts and 3 mol % of dimethyldiphosphine.

a2) Conversion of the sodium salts into the acids/NaCl removal

In succession, 60 g of 5% aqueous hydrogen peroxide solution, 240 g of 36% hydrochloric acid and 400 g of 2-ethylhexanol were added to the solution. After the water formed had been removed by distillation on a water separator, the precipitated sodium chloride was filtered off and washed with 100 g of 2-ethylhexanol.

b) Esterification of methanephosphonous acid in the reaction mixture

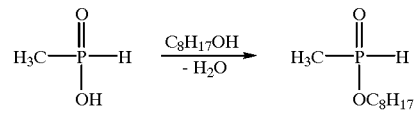

The ethylhexanol solutions from step a2) were combined and heated at about 120° C. for about 6 hours on a water separator under slightly reduced pressure.

c) Isolation of the ester

The esterified reaction mixture was subsequently freed from excess ethylhexanol by distillation and subjected to a vacuum distillation. At a pressure of 0.3 mm and a head temperature of 75° C., 220 g of 2-ethylhexyl methanephosphonite passed over. The product was obtained in the form of a clear, colorless liquid in a purity of greater than 99%, corresponding to a yield of 58%, based on the yellow phosphorus employed. Analyses: 16.0% of phosphorus (theory: 16.2%); $^{31}$P-NMR: doublet at 34 ppm (diastereomer pair).

Example 2

Addition of 2-ethylhexyl methanephosphonite onto hydroxyethyl acrylate (free-radical catalysis)

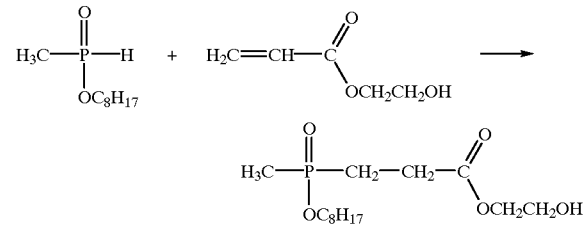

128.8 g (90.5%, 0.607 mol) of 2-ethylhexyl methanephosphonite and 0.2 g of Trigonox 25-C-75 are introduced into a 500 ml five-necked flask fitted with thermometer, reflux condenser, high-speed stirrer and dropping funnel and preheated to 80° C. 22.8 g of hydroxyethyl acrylate (0.2 mol) are added dropwise at 80° C. over the course of 30 minutes with stirring. The reaction is slightly exothermic. The mixture is subsequently allowed to react at 80° C. for a further 10 minutes. A pale yellow liquid is obtained. The $^{31}$P-NMR shows 21% of 2-ethylhexyl 2-hydroxyethyl-2-carboxyethylmethylphosphinate at 54 ppm and 77% of unreacted 2-ethylhexyl methanephosphonite (34 ppm). The unreacted 2-ethylhexyl methanephosphonite is removed by vacuum distillation at 0.1 mm and a head temperature of 80° C., giving 53.4 g of product having a purity of about 80%.

Example 3
Addition of 2-ethylhexyl methanephosphonite onto hydroxyethyl acrylate (anionic catalysis)

78.8 g (0.41 mol) of 2-ethylhexyl methanephosphonite and 47.6 g of hydroxyethyl acrylate are introduced into a 500 ml five-necked flask fitted with thermometer, reflux condenser, high-speed stirrer and dropping funnel. 5 ml of sodium methoxide (30%) are added dropwise, with stirring, at such a rate that a maximum reaction temperature of 120° C. becomes established. The mixture is subsequently allowed to react at 80° C. for a further 10 minutes. A pale yellow liquid is obtained. $^{31}$P-NMR (CHCl$_3$): 57 ppm.

Example 4
Addition of 2-ethylhexyl methanephosphonite onto acrylonitrile 107.4 g (0.559 mol) of 2-ethylhexyl methanephosphonite and 37.4 g of acrylonitrile are introduced into a 500 ml five-necked flask fitted with thermometer, reflux condenser, high-speed stirrer and dropping funnel. 4 ml of sodium methoxide (30%) are added dropwise, with stirring, at such a rate that a reaction temperature of 70° C. becomes established. The mixture is subsequently allowed to react at 80° C. for a further 10 minutes. A pale yellow liquid is obtained. $^{31}$P-NMR (CHCl$_3$): 53–54 ppm.

Example 5
Addition of 2-ethylhexyl methanephosphonite onto methyl acrylate 85 g (0.445 mol) of 2-ethylhexyl methanephosphonite and 43 g of methyl acrylate are introduced into a 500 ml five-necked flask fitted with thermometer, reflux condenser, high-speed stirrer and dropping funnel. 4 ml of sodium methoxide (30%) are added dropwise, with stirring, at such a rate that a reaction temperature of 80° C. becomes established. A pale yellow liquid is obtained. $^{31}$P-NMR (CHCl$_3$): 58 ppm.

Example 6
Addition of 2-ethylhexyl methanephosphonite onto dimethyl Itaconate 57.6 g (0.3 mol) of 2-ethylhexyl methanephosphonite and 47.4 g of dimethyl itaconate (0.3 mol) are introduced into a 500 ml five-necked flask fitted with thermometer, reflux condenser, high-speed stirrer and dropping funnel. 3 ml of sodium methoxide (30%) are added dropwise, with stirring, at such a rate that a maximum reaction temperature of 90° C. becomes established. The mixture is subsequently allowed to react at 50–70° C. for a further 1 hour. A pale yellow liquid is obtained. $^{31}$P-NMR (CHCl$_3$): 55–56 ppm.

Example 7
Addition of 2-ethylhexyl methanephosphonite onto acroleincyanohydrin acetate 155.3 g of 2-ethylhexyl methanephosphonite are introduced into a 500 ml five-necked flask fitted with thermometer, reflux condenser, high-speed stirrer and dropping funnel. 50 g of acroleincyanohydrin acetate and 4 g of t-butyl peroctanoate are added dropwise at 130° C. over the course of one hour with stirring. The mixture is then allowed to react at 120° C. for a further 15 minutes, and the product is subsequently distilled off in a high vacuum at 170° C. and 0.4 mbar, giving 112 g of 2-ethylhexyl (3-acetoxy-3-cyanopropyl)methylphosphinate.

What is claimed is:

1. A process for the preparation of phosphinic acid esters, which comprises
   a) reacting elemental yellow phosphorus with alkylating agents in the presence of a base to give a mixture which comprises, as principal constituents, the (metal) salts of alkylphosphonous, phosphorous and hypophosphorous acids,
   b) esterifying the principal constituents of the mixture from a) to give an ester mixture,
   c) isolating the ester of the alkylphosphonous acid from the ester mixture,
   d) adding the resultant ester of the alkylphosphonous acid onto an olefin containing a functional group.

2. A process as claimed in claim 1, wherein the alkylating agents are alkyl halides, dialkyl sulfates, trialkyl phosphates, dialkyl carbonates and/or formic acid ortho-esters.

3. A process as claimed in claim 1, wherein the alkylating agent employed is methyl chloride, methyl bromide and/or dimethyl sulfate.

4. A process as claimed in claim 1, wherein the bases are hydroxides, carbonates, bicarbonates, amides, alkoxides and/or amine bases.

5. A process as claimed in claim 1, wherein the reaction in step a) is carried out in a two-phase system comprising aqueous alkali or alkaline-earth metal hydroxide or mixtures thereof and an organic solvent.

6. A process as claimed in claim 1, wherein the organic solvents employed are straight-chain or branched alkanes, alkyl-substituted aromatic solvents, water-immiscible or only partially water-miscible alcohols or ethers, alone or in combination with one another.

7. A process as claimed in claim 1, wherein the organic solvent employed is toluene, alone or in combination with alcohols.

8. A process as claimed in claim 1, wherein the reaction is carried out in the presence of a phase-transfer catalyst.

9. A process as claimed in claim 8, wherein the phase-transfer catalyst is a tetraalkylphosphonium halide, triphenylalkylphosphonium halide or tetraorganylammonium halide.

10. A process as claimed in claim 1, wherein the temperature during the reaction with the yellow phosphorus is from −20 to +80° C.

11. A process as claimed in claim 1, wherein the temperature during the reaction with the yellow phosphorus is from 0 to 30° C.

12. A process as claimed in claim 1, wherein the reaction is carried out under a pressure of from 0 to 10 bar.

13. A process as claimed in claim 1, wherein the principal constituents of the mixture from a) are esterified in step b) using a linear or branched alcohol of the general formula R—OH, where R is a linear or branched alkyl radical having 1 to 10 carbon atoms.

14. A process as claimed in claim 1, wherein the principal constituents of the mixture from a) are reacted with mineral acids to give a mixture of alkylphosphonous, phosphorous and hypophosphorous acids and at the same time the (metal) salts of the mineral acids are precipitated, and the mixture of these acids is subsequently esterified.

15. A process as claimed in claim 1, wherein the water formed during the esterification is removed by azeotropic distillation.

16. A process as claimed in claim 1, wherein the alcohol is n- or i-butanol, n-hexanol, ethylhexanol and/or amyl alcohol.

17. A process as claimed in claim 14, wherein the mineral acid is hydrochloric acid, sulfuric acid and/or phosphoric acid.

18. A process as claimed in claim 14, wherein the mineral acid is hydrochloric acid.

19. A process as claimed in claim 1, wherein phosphines are formed in small amounts in step a), and wherein the phosphines formed in small amounts in step a) are removed by oxidation.

20. A process as claimed in claim 19, wherein hydrogen peroxide is employed for the oxidation.

21. A process as claimed in claim 1, wherein the ester of the alkylphosphonous acid is removed by distillation in step c).

22. A process as claimed in claim 1, wherein the ester of the alkylphosphonous acid is n-butyl methylphosphonite, isobutyl methylphosphonite, n-hexyl methylphosphonite, 2-ethylhexyl methylphosphonite and/or amyl methylphosphonite.

23. A process as claimed in claim 1, wherein the addition reaction in step d) is carried out in the presence of catalysts.

24. A process as claimed in claim 23, wherein the catalysts are basic catalysts.

25. A process as claimed in claim 23, wherein the basic catalysts are alkali metal and/or alkaline-earth metal alkoxides.

26. A process as claimed in claim 1, wherein the olefins containing functional groups are α,β-unsaturated carboxylic acid esters, chlorides, amides or nitriles, α,β-unsaturated ketones, alkyl vinyl sulfones and vinyl carboxylates.

27. A process as claimed in claim 1, wherein the olefins containing functional groups are α,β-unsaturated carboxylic acid esters of aliphatic or cycloaliphatic alcohols having 1 to 20 carbon atoms or carboxylic acid esters of polyhydric alcohols having 2 to 4 hydroxyl groups and 2 to 20 carbon atoms.

28. A process as claimed in claim 1, wherein the olefins containing functional groups are acrylic acid derivatives of the general formula (I)

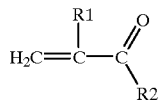

where R1 is CH$_3$ or H, and R2 is an ester group of a monohydric or polyhydric alcohol having 1–12 carbon atoms or an amino group.

29. A process as claimed in claim 1, wherein the olefins containing functional groups are acroleincyanohydrin compounds of the formula (II)

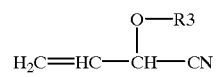

where R3=acetyl or propionyl.

30. A process as claimed in claim 1, wherein the olefins containing functional groups are itaconic acid derivatives of the general formula (III), where R'=alkyl group having 1–12 carbon atoms

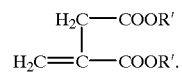

31. A process as claimed in claim 1, wherein the olefin is hydroxyethyl acrylate, methyl acrylate, ethyl acrylate, hydroxyethyl methacrylate, methyl methacrylate, ethyl methacrylate, dimethyl itaconate, diethyl itaconate and/or acroleincyanohydrin acetate.

32. A process as claimed in claim 1, wherein the alkylphosphonous acid is methanephosphonous acid.

33. A method for reactively flame retarding polymers using a phosphinic acid ester prepared by a process as claimed in claim 1, said method comprising providing a phosphinic acid ester prepared by a process as claimed in claim 1.

34. A method for reactively flame retarding polymers according to claim 33 further comprising selecting a thermoplastic polymer such as polyethylene terephthalate, polybutylene terephthalate or polyamide.

35. A method for reactively flame retarding polymers according to claim 33 further comprising selecting a thermosetting resins such as unsaturated polyester resins, epoxyresins, polyurethanes or acrylates.

36. A method for using a phosphinic acid ester prepared by a process as claimed in claim 1 as a precursor for chemical synthesis, said method comprising providing a phosphinic acid ester prepared by a process as claimed in claim 1.

37. A method for using a phosphinic acid ester prepared by a process as claimed in claim 1 in the preparation of organophosphorous compounds and derivatives, said method comprising providing a phosphinic acid ester prepared by a process as claimed in claim 1.

* * * * *